(12) United States Patent
Laitinen et al.

(10) Patent No.: US 8,742,367 B2
(45) Date of Patent: Jun. 3, 2014

(54) MULTI-PURPOSE MEASUREMENT SYSTEM

(75) Inventors: Jyrki Laitinen, Kuusisto (FI); Petri Kivelä, Piispanristi (FI)

(73) Assignee: Wallac Oy, Turku (FI)

( * ) Notice: Subject to any disclaimer, the term of this patent is extended or adjusted under 35 U.S.C. 154(b) by 182 days.

(21) Appl. No.: 12/739,144

(22) PCT Filed: Oct. 8, 2008

(86) PCT No.: PCT/FI2008/050560
§ 371 (c)(1),
(2), (4) Date: Apr. 22, 2010

(87) PCT Pub. No.: WO2009/056670
PCT Pub. Date: May 7, 2009

(65) Prior Publication Data
US 2010/0252748 A1    Oct. 7, 2010

Related U.S. Application Data

(60) Provisional application No. 61/001,120, filed on Oct. 31, 2007.

(51) Int. Cl.
| | |
|---|---|
| *G01N 21/64* | (2006.01) |
| *G01J 3/10* | (2006.01) |
| *G01J 3/44* | (2006.01) |
| *G01N 21/25* | (2006.01) |
| *G01J 3/42* | (2006.01) |
| *G01J 3/12* | (2006.01) |
| *G02B 6/42* | (2006.01) |
| *G01J 3/02* | (2006.01) |

(52) U.S. Cl.
CPC ............ *G01N 21/253* (2013.01); *G02B 6/4298* (2013.01); *G01N 2021/6484* (2013.01); *G01J 3/10* (2013.01); *G01N 2021/6439* (2013.01); *G01J 3/0218* (2013.01); *G01N 21/6452* (2013.01); *G01J 3/44* (2013.01); *G01N 21/6408* (2013.01); *G01J 3/42* (2013.01); *G01J 3/12* (2013.01); *G01N 2021/6491* (2013.01)
USPC ................................................... 250/458.1

(58) Field of Classification Search
CPC ............. G01J 3/4406; G01J 2003/106; G01J 2003/102; G01N 2021/6484; G01N 2021/6491
USPC .......................................... 385/22; 250/458.1
See application file for complete search history.

(56) References Cited

U.S. PATENT DOCUMENTS

| | | |
|---|---|---|
| 5,475,221 A | 12/1995 | Wang |
| 6,097,025 A | 8/2000 | Modlin |

(Continued)

FOREIGN PATENT DOCUMENTS

| | | | |
|---|---|---|---|
| EP | 1403675 Y | | 3/2004 |
| EP | 1517135 A | | 3/2005 |
| JP | 56004103 A | * | 1/1981 |

(Continued)

*Primary Examiner* — Constantine Hannaher
(74) *Attorney, Agent, or Firm* — Seppo Laine Oy; Joshua P. Wert

(57) ABSTRACT

An apparatus for optically analyzing samples contained in sample sites of a sample holder, the apparatus has a first light source and at least one second light source, a monochromator having an input to which first light source is optically connected or connectable and an output for monochromatized light, light guiding portion for guiding light originating from the first and from the at least one second light sources to the sample sites, and a detector for detecting light from the sample sites. A light relay having a first input optically connected to the output of the monochromator, at least one second input optically connected or connectable to a second light source such that the light from the second light source by-passes the monochromator, and a first output for guiding light from selected input of the light relay to the sample sites. Based on the apparatus and light relay a versatile sample analyzer can be achieved in a cost-effective manner.

20 Claims, 4 Drawing Sheets

(56) References Cited

U.S. PATENT DOCUMENTS

| | | |
|---|---|---|
| 2002/0060791 A1 | 5/2002 | Stumbo |
| 2005/0122521 A1 | 6/2005 | Katzlinger |
| 2007/0037135 A1 | 2/2007 | Barnes et al. |
| 2007/0247628 A1 | 10/2007 | Kivelä |
| 2008/0191149 A1* | 8/2008 | Zimenkov et al. ......... 250/492.1 |

FOREIGN PATENT DOCUMENTS

| | | |
|---|---|---|
| WO | WO 03027724 Y | 4/2003 |
| WO | WO 2009/056670 | 5/2009 |

* cited by examiner

MULTI-PURPOSE MEASUREMENT SYSTEM

BACKGROUND OF THE INVENTION

1. Field of the Invention

The invention relates to optical sample detectors used in various fields of life and analytical sciences, in particular medical and biomedical assays. In particular, the invention relates to sample analysers capable of fluorescence measurements.

2. Prior Art

Analysers of the present kind are commonly adapted to detect light successively from each one of a plurality of sample sites contained in the microplate. Therefore, they are frequently called as microplate "readers". One example or such a system is the EnVision-reader and its variants available from PerkinElmer.

The present commercial microplate readers typically include a broad-band excitation light source. Different kinds of optical arrangements for manipulating and guiding light from the light source to the sample sites are disclosed in US 2003/0081207, U.S. Pat. No. 6,232,608, WO 00/63680, US 2002/0109841, U.S. Pat. No. 6,313,471, WO 2005/057187, U.S. Pat. No. 6,097,025 and WO 2003/027724. For example, U.S. Pat. No. 6,097,025 discloses a measurement apparatus having a plurality of light sources and an optical path switching mechanism comprising a slidable shuttle.

U.S. Pat. No. 5,475,221 discloses an apparatus having an array of LEDs and an Acousto-Optic Tunable Filter (AOTF) controlled by multiplexing means to obtain a broadband spectrometer.

In addition BioTek Instruments Inc. has published a Synergy™ 4 Multi-Detection Microplate Reader. The system is provided with a Xenon flash as its light source and it combines both filter-based and quadruple monochromator-based fluorescence detection technology.

Each particular type of light source has its own advantages and disadvantages and allows for certain types of measurements, i.e. measurement modes, to be carried out. Moreover, a single light source can be used in several measurement modes, depending on how the light is guided to the sample and how light is collected from the sample. Apparatuses according to the prior art have the disadvantages that they are limited either to one light source or that the changing of light source used and/or the measurement mode is either difficult or accomplished in a complex way. Thus, the prior optical solutions are as such not well suitable for modern multi-purpose apparatuses intended to allow for carrying out diverse optical measurements in different optical configurations.

SUMMARY OF THE INVENTION

It is an aim of the invention to solve at least some of the above problems and to achieve a multi-purpose microplate reader while maintaining the complexity and costs of the apparatus at a reasonable level. In particular, it is an aim of the invention to achieve a novel measurement apparatus in which selection of measurement mode can be done in a reliable and accurate manner.

The invention is based in the idea of providing an apparatus for optically analysing samples contained in sample sites of a sample holder, comprising a first light source and at least one second light source, a monochromator having an input to which first light source is optically connected or connectable and an output for monochromatized light, light guiding means for guiding light originating from the first and from the at least one second light sources to the sample sites, a detector for detecting light from the sample sites, wherein the apparatus further comprises a light relay comprising a first input optically connected to the output of the monochromator, at least one second input optically connected or connectable to a second light source such that the light from the second light source by-passes the monochromator, and a first output for guiding light from selected input of the light relay to the sample sites.

According to one embodiment, the light relay further comprises a second output, the first and second outputs being adapted for guiding light from selected input of the light relay to the sample sites optionally from above or from below of the sample holder.

According to one embodiment, the light relay includes a plurality of light inputs arranged in circumferential manner to an input member and a plurality of light outputs arranged in circumferential manner on an output member. Further, the relay allows the inputs to be optically connected to the outputs one at a time, depending on the desired measurement mode, by the relative rotation of the input and output members.

According to one embodiment, the input member or the output member is a rotatable wheel comprising a plurality of connection slots for optic fibers.

According to one embodiment, the input and output members are arranged coaxially such that at least one of the inputs and one of outputs, respectively, can be optically connected to each other at a time. According to a further embodiment, a plurality of such input/output pairs can be formed at a time for providing two or more optical pathways.

The light source and light relay arrangement described above has the advantage that several different kinds of light sources can be conveniently incorporated into a single device without considerably increasing the amount of other optics in the device. Thus, the light relay acts as "an optical control centre" of the apparatus, guiding light to the measurement optics in a centralized manner. The measurement flexibility increases, as the optical relay may serve so as to guide light from the light sources to several measurement subunits, such as fluorescence measurement optics, absorption measurement optics, and/or to either the upper or lower side of the microplate.

A light relay having rotational structure can be manufactured to be very compact and is thus suitable for small measurement apparatuses. The design allows for versatile measurements because any one of the plurality of light sources can be easily and reliably connected to the sample sites from above or below. In addition, rotational movement is very accurate, which is of particular importance as the light guides are typically optical fibers which must be aligned with each other with good precision in order to avoid intensity losses.

The number of second light sources is typically 1-10, in particular 2-4.

It is another aim to provide a microplate reader which has an improved optical performance in contrast to known devices in the same price category. This is achieved by the embodiment, in which there are provided at the excitation side of the apparatus a plurality of narrow-band light sources having different emission bands, and a tuneable monochromator for further limiting the wavelength of the light conveyed to the sample. Further, the apparatus comprises means for conveying the light passing through the tuneable monochromator to a sample.

According to a one embodiment, the light sources are single-wavelength LEDs (light emitting diodes). The LEDs may be further arranged in a multiple-wavelength module, from which one optical signal at a time can be lead to the monochromator. The selection of the source LED is carried out using a optical switch separate from the LED module or by incorporating the LEDs into a combined light source/switching module.

The combination of narrow-band light sources, such as LEDs, and a single monochromator has proven to be surprisingly good as far as the amount of stray light hitting the sample and the costs of the device are concerned. The cost benefit results mainly from the fact that there is no need for second-order blocking of undesired wavelengths. This embodiment offers also the benefit that the excitation wavelength can be continuously selected, with the additional benefits of low cost, good performance and still the possibility to select the light source from a group of several light sources. Thus, the disadvantage of having to limit the possible excitation light at discrete wavelengths only, as when dichroic filters are used, is overcome. On the other hand, relatively inexpensive single monochromators can be used. Single monochromators provide monochromatization of the optical signal of only about 4 orders of magnitude, which is insufficient when used with broadband light sources. This is why prior art devices include additional band-limiting filters or double/tandem monochromators having two or more monochromators arranged in series.

By stating that two subunits of the apparatus are "optically connected or connectable", we mean that there is provided a direct optical link between the subunits, for example, by optical fibers or through direct visual connection, or that the device comprises means for easily connecting and disconnecting said link by suitable optical means, such as pivotable or movable mirrors, optical fiber connections, prisms or the like.

BRIEF DESCRIPTION OF THE DRAWINGS

The embodiments of the invention will be described more closely with reference to the attached drawings, in which.

DETAILED DESCRIPTION OF EMBODIMENTS

Figure 1:
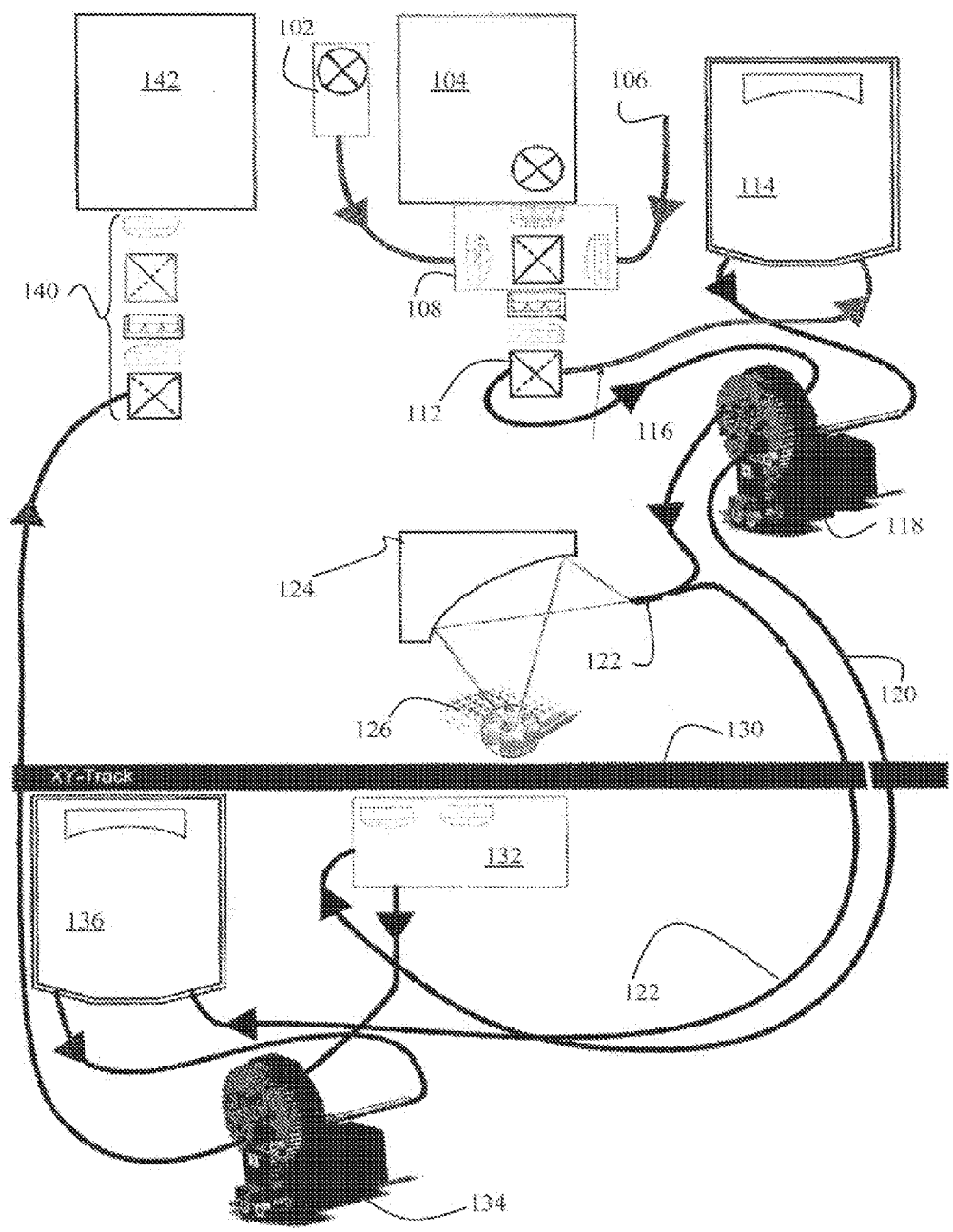
FIG. 1 represents an exemplary measurement set-up as a system-level scheme, including necessary equipment for both fluorescence and absorption measurements.

Referring to FIG. 1, the system comprises a multiple narrow-band light source module 102, which is used in fluorescence measurements. The module 102 is connected by an optical fiber or fiber bundle to a first light source selector module 108. To the first selector module 108 is also connected a wide-band light source 104. In this example, the selector module comprises also a third input 106 for a third light source type. The light is directed to a movable mirror 112, which is used for choosing the mode of operation. In absorbance measurements, wide-band light is conveyed to a sample site of a microtiter plate 126. In fluorescence measurement, narrow-band light is conveyed to a monochromator 114, from which the light is further guided to the sample site of the microtiter plate 126.

For selecting whether the absorption/excitation light is directed to the sample site from above or from below, a light relay 118 is provided in the optical path between the mirror 112 and the microtiter plate 126. Accordingly, the apparatus is provided with means for collecting the transmission/emission light from the sample sites. Such means may comprise a concave light-focusing mirror 124, as in the present example on top of the sample sites, or a lens element 132, as in the present example below the sample sites. In fluorescence measurements, the emission light is directed to a second monochromator for preventing wavelengths outside the region of interest to be blocked. In absorption measurements, the transmitted light is not conveyed to the monochromator. A second light switch 134 may be provided in order to optically connect the transmission/monochromatized emission light to a detector 142. Suitable optical means 140, such as mirrors, lenses and collimators may be provided before the detector.

The sample holder is schematically denoted with the reference numeral 130 in the Figure. The sample holder is adapted to move two-dimensionally (on XY-track) between the excitation/emission optics such that any of the plurality of sample sites contained in a microtiter plate placed on the holder can be subjected to measurement.

Figure 2:
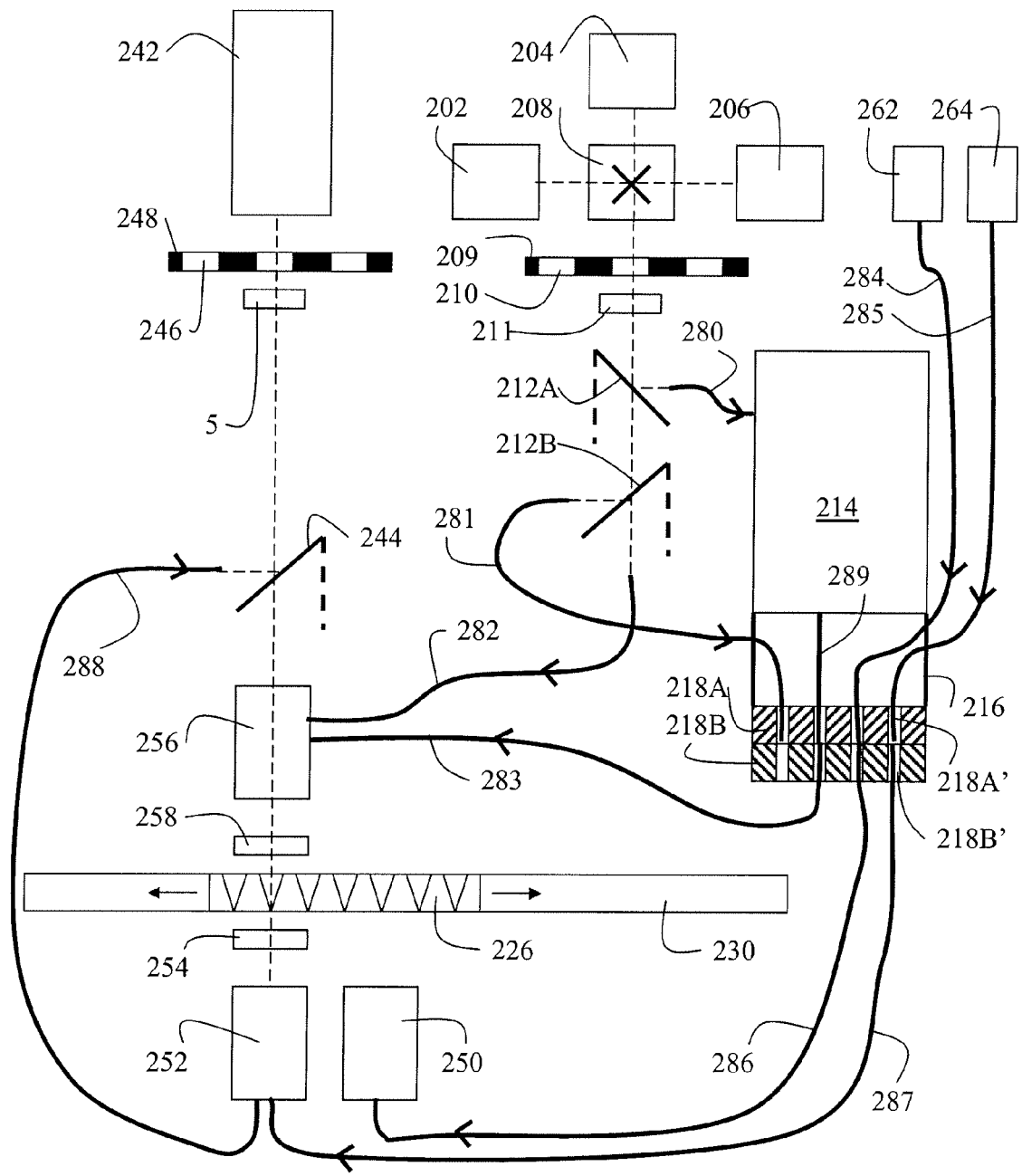
FIG. 2 illustrates another embodiment of the system.

With reference to FIG. 2, according to one embodiment of the invention the apparatus comprises as the first light source 202 a narrow-band light source, in which the wavelength is either tunable or selectable from a plurality of predefined alternatives. Light emitted by the first light source 202 is guidable to a monochromator 214 via optical fiber 280 for further reducing the wavelength band of the light. From the monochromator 214, monochromatized light is guided via optical fiber 289 to a first input of a light relay 218.

The input side of the light relay comprises an input member 218A, which contains a plurality of inputs 218A' and the output side of the light relay comprises an output member 218B, which contains a plurality of outputs 218B'. Further, the input member 218A and the output member 218B are movable with respect to each other such that at least one of the inputs 218A' in aligned with at least one of the outputs 218B' at a time for providing and optical connection between them. Also several such connections may be formed at a time.

The apparatus comprises means for guiding light from the light relay 218 successively to each of the sample sites of the sample plate 226 and for detecting light individually from said sample sites is turn. For this purpose, the sample plate 226 may be movable in two dimensions for allowing measurement of all sample sites of the sample plate 226. For this purpose, there may be provided a XY-track 230.

From the output side of the light relay 218, light is guided, depending on the measurement mode, either to upper or to lower side of the microtiter plate 226 for upper or lower sample excitation, respectively. In FIG. 2, the optical fiber 283 is used for upper excitation and the optical fiber 287 for lower excitation. Optical blocks 256, 252, respectively, are provided for directing the light excitation light towards the sample well to be measured. They also allow emission light to be passed to a detector 242. For this purpose, the blocks 256, 252 may contain a hinged or semitransparent mirror or the like optical arrangement. Lenses 258, 254 are typically provided between the blocks 256, 252 for giving the light beam hitting the sample a desired shape.

On emission side of the device, there are means for collecting the light emitted by the sample due to the excitation, and means for detecting the intensity of the collected light. The emission light collected from the sample by the upper of lower optical block 256, 252, depending on the measurement mode, is guided by to the detector 242. As the detector typically has only one input route, there may be provided a hinged or semitransparent mirror 244. In this example, emission light collected from below the plate 226, is guided via an optical fiber and reflected from the mirror 244, which is in first position, to detection optics. Emission light collected from above the plate 226 is guided directly to the detection optics. The detection optics may comprise a lens 245 and a filter bank 248 containing a plurality of emissions filters 246.

As illustrated in FIG. 2, the apparatus may comprise also one or more second light sources 204, 206, 262 and 264. These may include one or more wide band or monochromatic light sources, or both. The wide band light sources are arranged such that their emission light is guided to the optical relay partially along the sample optical path than light from the first light source, that is, in a light source entity comprising only unmonochromatic light sources. For this purpose, there may be provided a light source selector 208 having a turnable mirror or mirrors. Light from the wide band light sources is typically used for absorption/transmission measurements, whereby it is guided to the samples unmonochromatized. For achieving this, there is provided a first hinged mirror 212A, which can be placed in a position that reflects light either to the monochromator (first light source used) or directly to the light relay (second light source used). Further, there may be provided a second hinged mirror 212B, whose purpose is to guide light to the light relay or directly to the upper of lower optical block 256, 252, thus by-passing both the monochromator and the light relay.

According to one embodiment, the apparatus comprises at least one wide band second light source 204, 206, and at least one monochromatic second light source 262, 264. According to a further embodiment, the apparatus comprises both a continuous and a flashing second wide band source, such as a Cermax unit and a Xenon flash. According to a further embodiment, the apparatus comprises both a continuous and a pulsed monochromatic second light source, such as a laser.

There may be provided, before the monochromator 214, optics, such as a lens 211 and a filter bank 209, which comprises one or more individual filters 210. The purpose of these filters is to allow selection of more exact wavelength band of the wide band second light sources, that may be present.

Figure 3:
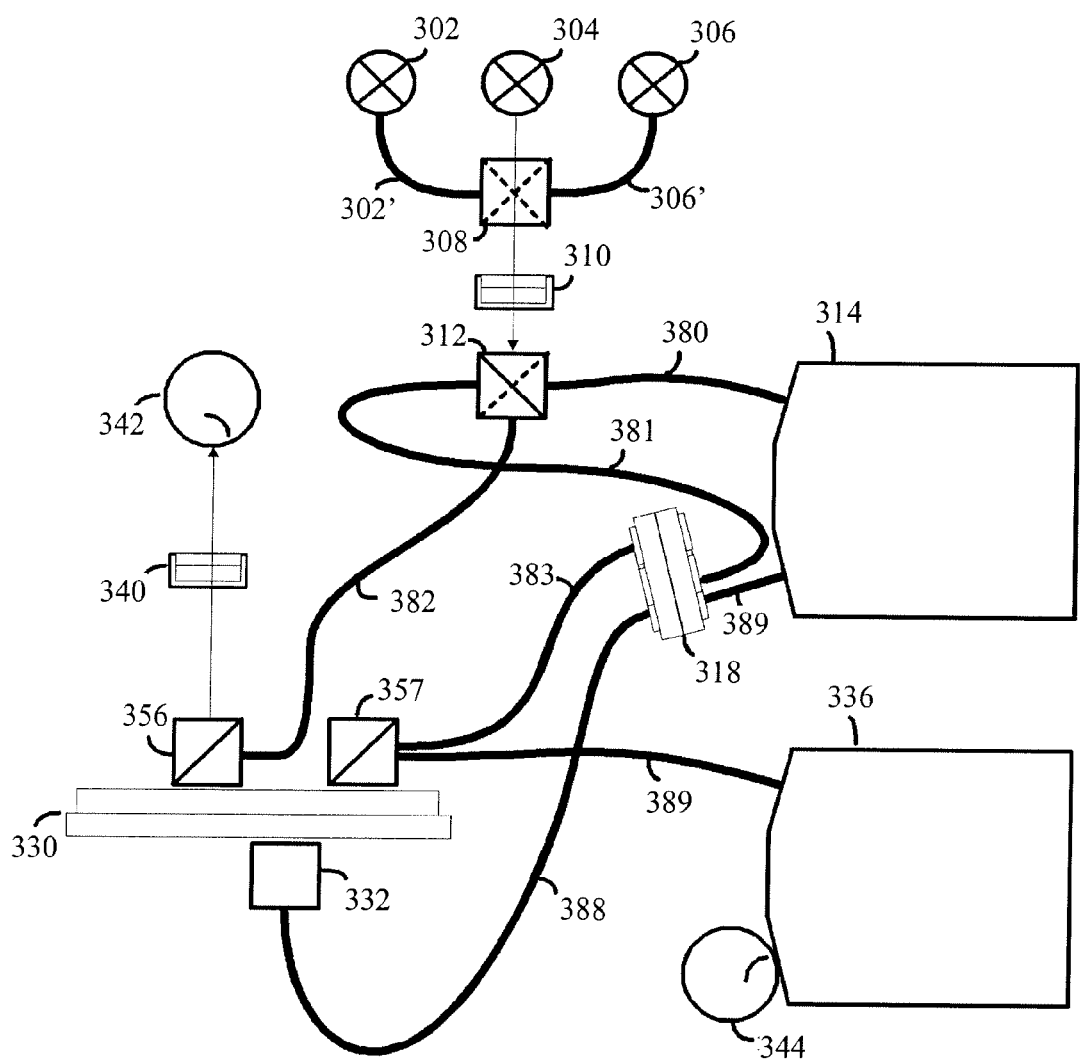
FIG. 3 illustrates still another embodiment of the system.

FIG. 3 illustrates still another embodiment of the system. The reference numerals 3xx mainly correspond to those of FIG. 1 (1xx). However, in this system, the light relay and one light detector on the emission side of the device is replaced with two individual light detectors 344 and 342, from which the first is connected to a monochromator and the other one is not. This allows for more versatile measurements, as detectors having different properties can be used.

As illustrated in FIG. 3, the apparatus may comprise an optics module 357 placed typically on top of the sample plate and comprising an input for excitation light (from fibre 383) and an output for emission light (to fibre 389). According to one embodiment, the optics module 357 comprises an excitation lens for focusing the excitation light to an individual sample space of the sample plate and an emission lens, separate from the excitation lens, for collecting emission light from the sample space. That is, the excitation and emission light are conveyed through separate optical channels in the optics module 357. However, there may be provided also one or more mirrors in the optics module that is/are common to both channels. In addition to focusing lenses, the channels may separately also contain mirrors and/or optical fibres.

As illustrated in FIG. 3, according to one embodiment, the output fibre of the optics module 357 is connected to an output monochromator 336 and further to the detector 344. The detector 344 downstream the monochromator 366 may also be employed for detecting emission light excited through a second optics module 332 placed below the sample plate and collected using the first optics module 357. On the other hand, the other detector 342 not typically coupled to a monochromator may be used to detect emission light excited through fibres 382 or 388 or in absorption measurements using, for example, the fibre 388 for transmitting broadband light to the sample through the second optics module 388 and collecting the transmitted light by a third optics module 356. It is clear from FIG. 3, that the optical relay 318 is the key element, in addition to the light source and light source selecting arrangement 302-314, in selecting the desired measurement mode out of the several possibilities herein described.

The present embodiments allow several kinds of measurements can be carried out, including fluorescence and time-resolved fluorescence, absorption, transmission, AlphaScreen using one apparatus only.

As the light initially has relatively narrow band (100 nm at maximum measured at 10% level), we have found that a single monochromator is sufficient for producing high-quality light whose wavelength can be selected not to overlap significantly with the emission wavelength of the sample. A single monochromator has the benefit of keeping the costs of the device at lower level. Of course, double or higher order monochromators can be used too. Such monochromators may be desirable, if also light from a wide-bandwidth lamp, such as a flash lamp (e.g. Xenon) or continuous lamp (e.g. Cermax) or the like is to be monochromatized by the monochromator by a suitable light-guiding arrangement.

Output of the monochromator is connected to the first input the light relay. For this purpose, there may be provided an optically transparent quartz bar or the like rigid light guide. According to one embodiment, the monochromator and the optical relay are formed as a single unit, wherein there is a direct optical visibility between the output of the monochromator and the first input of the relay.

The light relay comprises a first input optically connected to the output of the monochromator, and at least one second input optically connected (by direct optical fiber 284 or 285) or connectable (by means of the hinged mirror 212A) to a second light source. As shown in FIG. 2, one or more of the outputs of the light relay are in optical connection to the sample sites for providing measurement light therein. According to one embodiment the light relay comprises two outputs being adapted for guiding light from selected input of the light relay to the sample sites optionally from above or from below of the sample plate 226.

According to one embodiment, the light directed to the sample can be individually selected to originate from one of the light sources at a time. According to one embodiment, the inputs 218A' of the light relay are arranged in circumferential manner to an input member 218A and the outputs 218B' of the light relay are arranged in circumferential manner on an output member 218B facing the input member 218A and being rotatable with respect to the input member 218A for achieving selection of light to be guided to the sample sites. According to a further embodiment, the input and output members 218A, 218B are arranged coaxially such that at least one of the inputs and one of the outputs, respectively, can be optically connected to each other at a time. The input member 218A or the output member 218B, typically the output member 218B, may comprise a gearing, toothing or the like, which is connected to an electrically actuated motor, such as a stepper motor, for rotating the member into a desired position.

According to one embodiment, the optical relay allows the inputs 218A' of the light relay to be optically connected freely with any of the outputs 218B' of the relay one at a time, depending on the desired measurement mode. In some special measurement modes, also several outputs may be utilized at a time.

Light is guided to the inputs 218A' of the optical relay 218 and from the outputs 218B' of the optical relay 218 by means of optical fibres, whose ends can be aligned with each other in order to provide optical connection between a selected input and a selected output. The diameter of the input fibres is optionally chosen to be smaller than the diameter of output fibres. Thus, all light emitted by the ends of the input fibres is collected by the output fibres. In particular, when a rotating light relay construction is used, this feature has been found to be of importance for securing lossless light transmission through the light relay 218, because of the achievable tolerances of the rotation mechanics and overall thinness of the fibres According to one embodiment, the monochromator 214 and the optical relay 218 are in firm mechanical contact with each other. That is, they are mounted in fixed position relative to each other. This allows a special kind of optical connection between the units, namely by a rigid optical fiber, such as a quartz rod. This is beneficial, as it makes the optical connection between the units very robust. Manufacturing these units as a single mechanical entity allows also control electronics of the monochromator and the light relay to be manufactured in a single control unit located in their vicinity.

It has become apparent from the above that the apparatus may include a cascade of light source selectors: one in the first light source for choosing the individual narrow band light source; one downstream the first light source for selecting whether the first light source or some other light source is used; and one (the light relay) for finally choosing the desired measurement mode. It has shown that this kind of arrangement provides cost-effective manufacture, and versatile and flexible use of the device, allowing not only fluorescence measurement, but also other types of common measurements.

Figure 5:
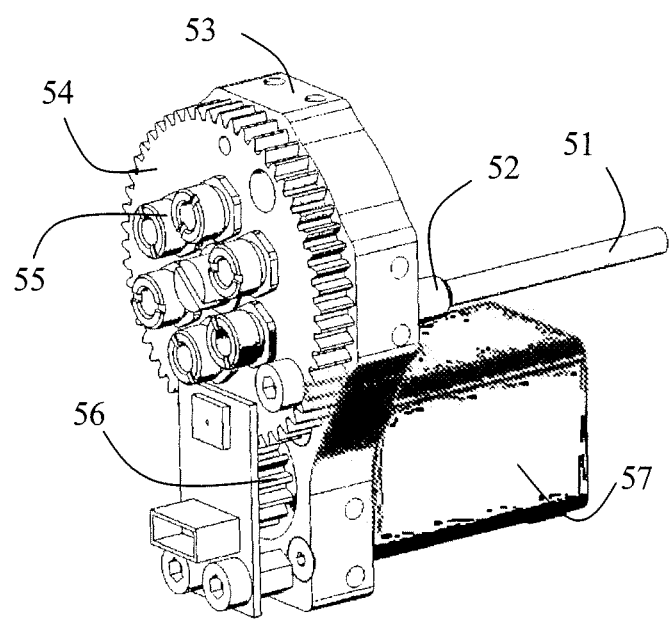
FIG. 5 illustrates in a perspective view in detail the light relay according to one embodiment of the invention.

FIG. 5 shows an exemplary embodiment of the optical relay which can be used for changing the mode of operation of the device (i.e., a relay corresponding to parts 118, 218 and 318 of FIGS. 1, 2 and 3, respectively). The relay comprises body 53, which comprises a plurality of inputs. Show in the figure is input 52, to which a quartz rod 51 from the excitation monochromator is connected. On the output side there is a toothed output wheel 54, which is rotatable. The rotation is achieved by rotating a toothed gear wheel 56, which co-operates with the output wheel 54. The gear wheel 56 is rotatably connected to a stepper motor 57. A plurality of outputs 55 are arranged on the output wheel 54. The outputs 55 are suitable for engagement with optical fibers or optical fiber connectors.

The first light source may comprise a plurality of light-emitting diodes having narrow (but not monochromatic) wavelength bands, typically 30-70 nm at 10% intensity level. Further the light source is provided with means for selecting light from only one of the light-emitting diodes to be passed out of the first light source, and further to the monochromator.

The narrow-band light sources within the first light source may be light-emitting diodes (LEDs), the emission bands of which are less than 100 nm, typically 30-70 nm (at 10% intensity level). According to one embodiment, the emission bands of the LEDs at least slightly overlap with each others emission bands. That is, the wavelength bands of at least two of the plurality of LEDs overlap, the light intensity at the overlap wavelength being at least 10% of the peak wavelength of the dimmer or the LEDs. If two or more LEDs are arranged this way, a continuous emission light spectrum on a range having a width of at least 100 nm, typically at least 200 nm, even more than 500 nm, can be produced by choosing a right LED for light production. Together with using a single tunable monochromator, this embodiment practically allows for selection of any narrow wavelength within that range to be used for excitation of the sample. The excitation light has been found to be of high quality. That is, practically no light is directed to the sample at its emission wavelength. The excitation and emission wavelengths of typical markers used in biomedical analyses differ from each other by 10-100 nm.

Both ultraviolet and visible light sources can be used within the present invention either separately or in combination. According to one embodiment, the LEDs substantially cover the wavelength range 260-1000 nm, in particular 365-940 nm, typically at least 450-600 nm. Thus, the most common excitation wavelengths of marking agents can be covered. According to one embodiment, there are provided LEDs having peak wavelength at one, several or all of the following: 365 nm, 375 nm, 450 nm, 460 nm, 500 nm, 525 nm, 590 nm, 630 nm, 640 nm. Typically LEDs of the "Power LED"-type are used.

For the spectrum achievable using a light source comprising a series of Philips Luxeon III Star power LEDs and for further details of the characteristics of the LEDs, see Technical Datasheet DS46/Luxeon/Philips. Another usable LED series for the present device are the Nichia Power LED series, which also cover UV wavelengths (e.g. the i-LED series).

Figure 4:
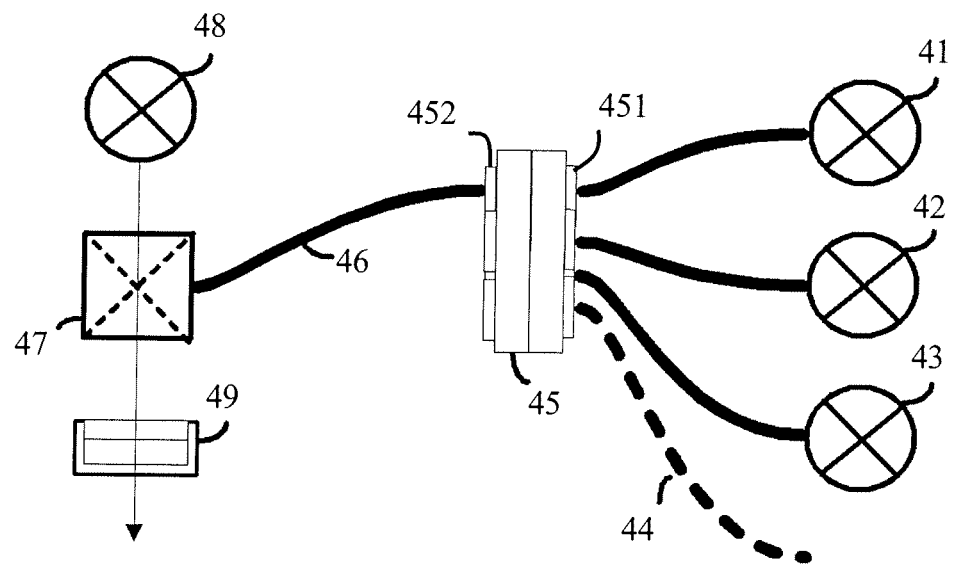
FIG. 4 depicts a multiple-narrow-band light source usable in the present system.

With reference to FIG. 4, the first light source comprises means for selecting which one of the individual light sources is optically coupled to the sample sites. According to one embodiment, the individual light sources 41, 42, 43 (optionally also more) are optically connected by means of optical fibers to a narrow band light source selector unit 45 that provides an optical pathway between one of the optical fibres and the output 452 of the first light source. There may be one or more further input channels 44 for additional individual light sources (in addition to the three explicitly illustrated in FIG. 4). The output 452 may also comprise a fiber optic connection 46 to further optics of the device (that is, typically another light source selector 47, corresponding to the light source selectors 108, 208, 308 introduced with reference to FIGS. 1, 2 and 3, respectively). The individual light sources 41, 42, 43 may be mounted on a separate light source module having an optical fiber connector for each of the individual light sources 41, 42, 43.

The narrow band light source selector may comprise a first rotating or translating element and a second static element, whereby the selection of the light source is determined by the relative positions of the first and second elements. For example, the ends of the optical fibres can be mounted circumferentially on an input wheel, which is rotatable such that one of the fibers at a time is aligned with an output fibre. Alternatively, the output fibre may be movable. Such an arrangement is illustrated in FIG. 4, wherein the inputs 451 and output 452 are mounted on elements, whish may be rotatable or translatable with respect to each other such that the mutual optical connection between the light sources 41, 42, 43 and the output 452 changes.

The plurality of light sources can also be directly mounted on a movable (typically translatable or rotatable) frame, whereby each one of the light sources can be individually optically coupled with the sample sites by movement the movable frame, for example, by aligning the light source with an output fibre, one end of which is arranged in the vicinity of the frame.

The light source used for excitation, i.e., in the exemplary embodiment the LED used, is chosen based on the properties of the marker agent used in the sample. That is, the emission wavelength band of the source is such that it covers the absorption wavelength of the marker but does not overlap with the emission wavelength of the marker. In practice, an optimization algorithm taking into account both these criteria may be used such that the best possible signal-to-noise ratio is achieved.

According to one embodiment, the excitation monochromator is a tunable single monochromator, in contrast to double or tandem monochromators typically used in high-performance plate readers.

According to one embodiment, a light switch is provided also on the emission side in order to allow for selecting a light detector most suitable for the intensity and/or wavelength of the emitted light and/or the goals of the measurement. Thus, a plurality of detectors may be used.

The emission side typically has a second monochromator for efficiently picking from the emission signal the marker emission wavelength of interest.

The monochromators on the excitation and on the emission sides can be diffraction grating-based tunable monochromators. For example, Czerny-Turner monochromators are suitable for the purposes of the invention. On the excitation side the tuning range of the monochromator typically extends over the usable bandwidth range of the narrow-band light sources.

Because grating-based monochromators, as is commonly known, pass through also higher diffraction order wavelengths, a filter or filters may be provided to prevent these undesired wavelengths from propagating to the sample. According to one embodiment, the apparatus automatically selects a right band-pass filter, depending on the wavelength of the narrow-band excitation light source used, for preventing any expected higher order interfering radiation. However, conventional band-pass filters are in one embodiment of the invention not used for any other purpose.

The use of LEDs in combination with a single monochromator offers significant benefits, as we have found that a very clean excitation light can be formed at a significantly reduced cost level. The quality of the excitation light reflects to the emission (detection) side of the device as a more marker-specific emission signal. Ultimately, the throughput rate of the apparatus can be improved as the measurement time of a single sample well can be kept short.

According to one embodiment, the device comprises, as far as their wavelength band in concerned, three types of different light sources: a multiple narrow-band light source (the first light source), a wide bandwidth light source and a monochromatic light source. Light from all these is guided or guidable to the sample sites through the light relay as described above in detail. Thus, the light relay guides light to the measurement optics in a centralized manner.

According to one embodiment, the detector of the apparatus is a photomultiplier tube (PMT). Other kinds of detectors may be employed too.

Also several detectors may be arranged in parallel and means for optically switching between the detectors may be provided. This allows for the most suitable detector for the wavelength/intensity to be used.

The embodiments described above and presented in the attached drawings are provided for illustrative purposes and do not limit the scope of the invention defined in the appended claims. The embodiments may be combined in order to achieve even more versatile systems. In particular, the light source arrangements, in particular, teachings concerning the structure and operation of the multiple-narrow-band light source, as well as the structure and operation of the light relay for selecting the operation mode of the device can be freely applied to each of the exemplified embodiments and also those variations not herein discussed in detail.

The invention claimed is:

1. An apparatus for optically analysing samples contained in sample sites of a sample holder, comprising
   a first light source and at least one second light source,
   a monochromator having an input to which first light source is optically connected or connectable and an output for monochromatized light,
   light guiding means for guiding light originating from the first and from the at least one second light sources to the sample sites,
   a detector for detecting light from the sample sites,
   wherein the apparatus further comprises a light relay comprising
   a first input optically connected to the output of the monochromator,
   at least one second input optically connected to a second light source such that the light from the second light source by-passes the monochromator, and
   a first output and a second output adapted for guiding light from selected input of the light relay to the sample sites optionally from above or from below of the sample holder,
   and wherein the inputs of the light relay are arranged in circumferential manner to an input member and the outputs of the light relay are arranged in circumferential manner on an output member facing the input member, the input member or output member being rotatable for selecting the light source optically connected to the sample sites.

2. The apparatus according to claim 1, wherein the input and output members are arranged coaxially such that at least one of the inputs and one of outputs, respectively, can be optically connected to each other at a time.

3. The apparatus according to claim 1, wherein the input member or the output member further comprises a gearing which is connected to an electrically actuated motor for rotating the member into a desired position.

4. The apparatus according to claim 1, wherein the relay allows the inputs of the light relay to be optically connected freely with any of the outputs of the relay one at a time, depending on the desired measurement mode.

5. The apparatus according to claim 1, wherein the output of the monochromator is optically connected to the first input of the light relay by a rigid optical fiber, such as a quartz rod.

6. The apparatus according to claim 1, wherein the light relay is directly mounted to the monochromator in a fixed position.

7. The apparatus according to claim 1, wherein light is guided to the inputs of the light relay and from the outputs of the light relay by means of optical fibres, whose ends can be aligned with each other in order to provide optical connection between a selected input and a selected output, the input fibres being optionally smaller in diameter than the output fibres.

8. The apparatus according to claim 1, wherein the first light source comprises
   a plurality of light-emitting units, such as light-emitting diodes, having narrow wavelength bands, and
   means for selecting light from only one of the light-emitting units to be guided to the monochromator.

9. The apparatus according to claim 8, comprising means for automatically selecting the light-emitting unit used based on given properties of a marker agent used in the sample, the emission wavelength band of the source being such that it covers the absorption wavelength of the marker but does not significantly overlap with the emission wavelength of the marker.

10. The apparatus according to claim 1, wherein at least one of the second light sources is optically connectable to the input of the monochromator.

11. The apparatus according to claim 1, wherein at least one of the second light sources comprises a wide-bandwidth light source, such as a Xenon flash or a Cermax unit.

12. The apparatus according to claim 1, comprising means for optically connecting the first light source to a third input of the light relay such that the light by-passes the monochromator.

13. The apparatus according to claim 1 comprising at least two separate second light sources having different optical properties.

14. The apparatus according to claim 1, wherein at least one of the second light sources comprises a substantially monochromatic light source, such as a laser, optically connected to a second input of the light relay.

15. The apparatus according to claim 1 comprising a second monochromator for picking to the detector a wavelength of interest from light from the sample site.

16. An apparatus for optically analysing samples contained in a sample site of a sample holder, comprising;
    a first light source and a second light source,
    a light source selector for selectively conveying light from the first light source or the second light source,
    a monochromator having an input to which light conveyed from the first light source is optically connected or connectable and an output for monochromatized light,
    a light relay having a first input optically connected to the output of the monochromator, a second input optically connectable to the second light source such that the light conveyed from the second light source by-passes the monochromator, a first output and a second output adapted for guiding light from a selected input of the light relay to a sample site optionally from above or below a sample holder, and wherein the first and second input of the light relay are arranged in an input member, the first and second outputs of the light relay are arranged in an output member facing the input member, and the input member or output member are rotatable for selecting the light source optically connected to the first or second output,
    a light guiding means for guiding light conveyed from the first or from the second light source to the sample site, and
    a detector for detecting light from the sample site.

17. The apparatus of claim 16, further comprising at least one additional second light source, wherein the light source selector further selectively conveys light from said at least one additional second light source.

18. The apparatus of claim 17, further comprising at least one additional second light source, wherein said at least one additional second light source is connected to an additional second input of the light relay, and wherein said additional second input is arranged in the input member.

19. The apparatus of claim 16, further comprising at least one additional second light source, wherein said at least one additional second light source is connected to an additional second input of the light relay, and wherein said additional second input is arranged in the input member.

20. The apparatus according to claim 16, wherein the inputs of the input member are arranged circumferentially, the outputs of the output member are arranged circumferentially and the input member or the output member further comprises a gearing which is connected to an electrically actuated motor for rotating the member into a desired position.

* * * * *